(12) United States Patent
Birdsall

(10) Patent No.: US 9,927,408 B2
(45) Date of Patent: Mar. 27, 2018

(54) METHODS FOR INCREASING SENSITIVITY OF DETECTION AND/OR QUANTIFICATION OF NEGATIVELY CHARGED ANALYTES

(71) Applicant: Waters Technologies Corporation, Milford, MA (US)

(72) Inventor: Robert E. Birdsall, Southborough, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 15/389,744

(22) Filed: Dec. 23, 2016

(65) Prior Publication Data

US 2017/0184555 A1    Jun. 29, 2017

Related U.S. Application Data

(60) Provisional application No. 62/272,249, filed on Dec. 29, 2015.

(51) Int. Cl.
  *H01J 49/00* (2006.01)
  *G01N 30/72* (2006.01)
  *C12Q 1/68* (2018.01)

(52) U.S. Cl.
  CPC .......... *G01N 30/7273* (2013.01); *C12Q 1/68* (2013.01); *H01J 49/0031* (2013.01); *H01J 49/0036* (2013.01)

(58) Field of Classification Search
  CPC ..... G01N 30/72; G01N 30/7206; H01J 49/00; H01J 49/02; H01J 49/04; H01J 49/0404; H01J 49/0431

USPC .......................................... 250/281, 282, 288
See application file for complete search history.

(56) References Cited

U.S. PATENT DOCUMENTS 6,471,866 B1    10/2002 Gjerde et al.

FOREIGN PATENT DOCUMENTS

WO    WO-199922839 A1    5/1999

OTHER PUBLICATIONS

Erb et al., Comparison of Mobile-Phase Systems Commonly Applied in Liquid Chromatography-Mass Spectrometry of Nucleic Acids, 2014, Electrophoresis, 35, 1226-1235.*
Gilar et al., "Analytical Biochemistry", vol. 298, No. 2, Nov. 1, 2001, pp. 196-206.
Lingzhi Gong et al., "Rapid Communications in Mass Spectrometry", vol. 28, No. 4, Dec. 26, 2013, pp. 339-350.

* cited by examiner

*Primary Examiner* — Jason McCormack
(74) *Attorney, Agent, or Firm* — Womble Bond Dickinson (US) LLP; Deborah M. Vernon; Rebecca N. Barnes

(57) ABSTRACT

The present technology provides methods for increasing sensitivity of detection and/or quantification of a negatively charged analyte, e.g., an oligonucleotide, using an analytical system that comprises liquid chromatography and mass spectrometry. The methods comprise passing an acidic solution through the analytical system, i.e., through a fluidic path from the mobile phase reservoir to the detector to remove or displace, at least in part, metal ions adsorbed to charged sites in the fluidic path.

19 Claims, 8 Drawing Sheets

METHODS FOR INCREASING SENSITIVITY OF DETECTION AND/OR QUANTIFICATION OF NEGATIVELY CHARGED ANALYTES

RELATED APPLICATIONS

This application claims the benefit of U.S. Provisional Application No. 62/272,249, filed on Dec. 29, 2015, the entire contents of which are hereby incorporated herein by reference.

FIELD OF THE TECHNOLOGY

The present disclosure relates to methods for increasing sensitivity of detection and/or quantification of negatively charged analytes during analysis that employs ion-pairing reversed phase liquid chromatography (IP-RPLC) and mass spectrometry.

BACKGROUND OF THE TECHNOLOGY

It is often necessary to detect and/or quantify negatively charged analytes in various samples, such as biological samples. Of the negatively charged analytes, oligonucleotides are of a particular interest to the pharmaceutical industry as therapeutic agents. For example, oligonucleotides may be used therapeutically as sense/antisense deoxyribonucleic acid (DNA) oligonucleotides or as interfering ribonucleic acid (RNAi) oligonucleotides to inhibit proteins, or as nucleic acid based aptamers (McGinnis et al., *Journal of Chromatography B* 2012; 883-884:76-94; Agrawal and Zhao, *Current Opinion in Chemical Biology* 1998; 2:519-28; Lee et al., *Current Opinion in Chemical Biology* 2006; 10:282-9). This renewed interest has, in part, been fueled by the commercial success of therapeutic oligonucleotides, such as Formivirsen (Perry and Balfour, *Drugs* 1999; 57:375-80) and Pegaptanib (Gragoudas et al., *New England Journal of Medicine* 2004; 351:2805-16), in the treatment of cytomegalovirus retinitis and age-related macular degeneration, respectively.

Conceptually, synthetic therapeutic oligonucleotides are comprised of their corresponding base nucleic acids and are synthesized with fragment lengths typically ranging from 15 nucleotides (15' mer or 15 nt) and 30 nucleotides (30' mer or 30 nt), although fragments with more than 30 nt have also garnered increasing interest from the pharmaceutical industry (McGinnis et al., *Journal of Chromatography B* 2012; 883-884:76-94). Chemical modifications to the phosphodiester backbone are commonly incorporated into synthetic oligonucleotides to increase their stability in vivo against endo- and exonucleases, as well as improve efficacy through increased cellular uptake and binding (McGinnis et al., Journal of Chromatography B 2012; 883-884:76-94; Akhtar et al., *Life Sciences* 1991; 49:1793-801; Vaerman et al., *Blood* 1997; 90:331-9). While the process for oligonucleotide synthesis is well-controlled, several factors can alter the end product. Purity of the starting materials can affect sequence failure rate, while random insertions and deletions can result in improper sequence generation (Gilar and Bouvier, *Journal of Chromatography A* 2000; 890:167-77; Gilar, *Analytical Biochemistry* 2001; 298:196-206). Furthermore, base pair switches and the presence of chiral centers can result in difficulties in separating isomers and diastereomers, respectively (Dias and Stein, *Molecular Cancer Therapeutics* 2002; 1:347-55). With over a hundred therapeutic oligonucleotides currently in development or in clinical trials, factors such as safety, efficacy, and stability are leading concerns for pharmaceutical companies and regulatory agencies (McGinnis et al., *Journal of Chromatography B* 2012; 883-884:76-94). In this regard, analytical methods for robust and accurate detection and quantification of negatively charged analytes, such as oligonucleotides, are highly desirable.

The intrinsic negative charge of the phosphodiester backbone present in oligonucleotides, combined with their ultraviolet (UV) absorbance properties has made chromatographic based characterization methods, such as ion-exchange chromatography (IEC) and ion-pairing reversed phase chromatography (IP-RPLC), popular choices in the characterization of oligonucleotides (Waters et al., *Journal of Clinical Oncology* 2000; 18:1812-23; Arora et al., *Journal of Pharmaceutical Sciences* 2002; 91:1009-18; Bunček et al., *Analytical Biochemistry* 2006; 348:300-6; Huber et al., *Analytical Biochemistry* 1993; 212:351-8; Apffel et al., *Analytical Chemistry* 1997; 69:1320-5; McCarthy et al., *Analytical Biochemistry* 2009; 390:181-8).

Charge-based separations, such as anion exchange chromatography, are well suited for characterization of oligonucleotides containing N-X deletions, however, oligonucleotides containing apurinic sites, base inversion isomers, and other base modifications are not readily characterized using ion exchange chromatography (IEC; McGinnis et al., *Journal of Chromatography B* 2012; 883-884:76-94). Furthermore, buffers and salt gradients typically used in IEC prevent the coupling of IEC to mass spectrometry (MS), which may be useful as a complementary orthogonal technique for characterizing oligonucleotides containing difficult to analyze base modifications. Analytical techniques, such as ion-pairing reversed phase liquid chromatography (IP-RPLC), have become popular for characterizing oligonucleotides, in part due to their compatibility with MS based techniques. This was demonstrated by Apffel and colleagues using triethylamine (TEA) as the IP base buffered in hexafluoroisopropanol (Apffel et al., *Analytical Chemistry* 1997; 69:1320-5; Apffel et al., *Journal of Chromatography A* 1997; 777:3-21). Oligonucleotides may be separated with high separation efficiency using hydrophobic bonded phases with adsorbed n-alkyl IP reagents, such as amines, based on charge interactions of the phosphodiester backbone and, to a lesser degree, the secondary structure of the oligonucleotide and hydrophobicity of the base nucleotides (Gilar, *Analytical Biochemistry* 2001; 298:196-206; Huber et al., *Analytical Biochemistry* 1993; 212:351-8; Gilar et al., *Journal of Chromatography A* 2002; 958:167-82; Dickman, *Journal of Chromatography A* 2005; 1076:83-9). MS based methods can provide accurate mass information for oligonucleotides and are highly desirable for analyses that require high sensitivity, such as toxicology and metabolite studies, including determination of pharmacodynamics and pharmacokinetic parameters (Dias and Stein, *Molecular Cancer Therapeutics* 2002; 1:347-55; Huber et al., *Analytical Biochemistry* 1993; 212:351-8; Zhang et al., *Analytical Chemistry* 2007; 79:3416-24; Deng et al., *Journal of Pharmaceutical and Biomedical Analysis* 2010; 52:571-9; Beverly et al., 2005; 19:1675-82). There are, however, challenges associated with the MS based techniques for the analysis of negatively charged analytes, such as oligonucleotides (Lin et al., *Journal of Pharmaceutical and Biomedical Analysis* 2007; 44:330-41; Cech and Enke, *Mass Spectrometry Reviews* 2001; 20:362-87; Keller et al., *Analytica Chimica Acta* 2008; 627:71-81; Ende and Spiteller, *Mass Spectrometry Reviews* 1982; 1:29-62).

One of such challenges involves contamination of the analytical system with alkali metal ions. There are several possible ways for the analytical system to become contaminated with alkali metal ions. For example, alkali metal oxides are used in the manufacturing process of laboratory glassware, such as borosilicate glassware, and can leach into solvents over time in the presence of acids, bases and organic solvents (Varshneya, Fundamentals of inorganic glasses, Elsevier, 2013). Similarly, metal surfaces throughout the fluidic path can potentially leach metal ions via corrosion that occurs when the metal surfaces are exposed to acids and bases commonly used in LC separations. Alternatively, the impurities present in the solvents and reagents can also contribute to adduct formation in LC/ESI-MS based separations.

Electrospray ionization (ESI) MS based techniques commonly used in oligonucleotide analyses are known to be sensitive to alkali metal adduct formation (Apffel et al., *Analytical Chemistry* 1997; 69:1320-5; Zhang et al., *Analytical Chemistry* 2007; 79:3416-24; Huber et al., *Analytical Chemistry* 1999; 71:3730-9). Positively charged cations of alkali metal salts, such as sodium ($Na^+$) and potassium ($K^+$), are electrostatically attracted to the negatively charged polyanionic backbone of oligonucleotides (Muddiman et al., *J. Am. Soc. Mass Spectrom.* 1996; 7:697-706; Cheng et al., *Analytical Chemistry* 1995; 67:586-93). Alkali metal adducts, which can occur singly, multiply, or as any combination as shown in Table 1 below, directly impact the sensitivity of MS based analyses, because the available charge is distributed across the parent ion and the adducts. This problem becomes further compounded for longer oligonucleotides, because length of the sequence, the number of observed charge states, and base modifications can impact the degree of adduct formation and spectral complexity (Fountain et al., *Rapid Communications in Mass Spectrometry* 2003; 17:646-53; Gong and McCullagh, *Rapid Communications in Mass Spectrometry* 2014; 28:339-50).

TABLE 1

Formula for predicting charge states of alkali metal adducts of oligonucleotides analyzed in negative scan mode using ESI-MS. Molar masses of hydrogen (H), sodium (Na), and potassium (K) are 1.008 g/mol, 22.9898 g/mol and 39.0983 g/mol, respectively.

| Adduct Ion Composition | Predicted m/z Value |
|---|---|
| $[M - H]^-$ | $M - 1$ |
| $[(M - H) + Na]^-$ | $(M - 1) + 23$ |
| $[(M - H) + K]^-$ | $(M - 1) + 39$ |
| $[M - xH]^{-X}$ | $(M - xH)/x$ |
| $[(M - xH) + yNa]^{-X}$ | $[(M - xH) + 23y]/x$ |
| $[(M - xH) + yK]^{-X}$ | $[(M - xH) + 39y]/x$ |
| $[(M - xH) + yNa + zK]^{-X}$ | $[(M - xH) + 23y + 39z]/x$ |

Current strategies for reducing the extent of alkali metal adducts formation during oligonucleotide analysis with ESI-MS included the use of offline and online desalting procedures with varying success. Offline desalting procedures that incorporate the use of hydrophobic resins, molecular weight cutoff filters, and solid phase extraction techniques have been shown to be effective in reducing adduct formation (Gilar and Bouvier, *Journal of Chromatography A* 2000; 890:167-77; Ragas et al., *Analyst* 2000; 125:575-81; Bayer et al., *Analytical Chemistry* 1994; 66:3858-63; Deroussent et al., *Rapid Communications in Mass Spectrometry* 1995; 0:1-4; Jiang and Hofstadler, *Analytical Biochemistry* 2003; 316:50-7). However, the additional sample preparation steps required are not readily amendable to high-throughput platforms. Online desalting strategies have included incorporation of microdialysis or cation exchange chromatography (Muddiman et al., *Analytical Chemistry* 1996; 68:3705-12; Huber and Buchmeiser, *Analytical Chemistry* 1998; 70:5288-95). These techniques, while more amendable to high throughput methods, can increase instrument configuration complexity and require additional method re-conditioning/equilibration steps which can impact productivity. A more appealing alternative to reducing alkali metal adducts in oligonucleotide analyses has been to use sample additives that act as cation scavengers or work to suppress adduct formation via displacement mechanisms. For example, Limbach and colleagues observed that the addition of trans-1, 2-cyclohexanediaminetetraacetic acid monohydrate (CDTA), a metal chelator, reduced adduct formation in the analysis of RNA (Limbach et al., *J. Am. Soc. Mass Spectrom.* 1995; 6:27-39). Alternatively, addition of base, such as piperidine or TEA, was found to suppress adduct formation (Muddiman et al., *J. Am. Soc. Mass Spectrom.* 1996; 7:697-706; Cheng et al., *Analytical Chemistry* 1995; 67:586-93; Greig and Griffey, *Rapid Communications in Mass Spectrometry* 1995; 9:97-102). In contrast to Limbach et al., an extensive study by Gong and McCullagh of IP reagents buffered with HFIP found that metal chelators, such as CDTA and ethylenediaminetetraacetic acid (EDTA), did not have a significant impact on adduct formation (Gong and McCullagh, *Rapid Communications in Mass Spectrometry* 2014; 28:339-50). Their work indicated that adduct formation was dependent on oligonucleotide size. Interestingly, with the exception of the 10 nt polyT sequence, more than 25% of the MS signal was in a metal adduct form. Despite these conflicting reports, the relevance of suppressing cation adduction is evident in the diversity of strategies employed across instrument configurations and experimental settings.

These approaches, while effective in reducing metal adduct formation, do not address contribution of the instrument to metal salt adducts formation, a challenging task considering the ubiquitous nature of alkali metal salts in LC separations (Keller et al., *Analytica Chimica Acta* 2008; 627:71-81; Ende and Spiteller, *Mass Spectrometry Reviews* 1982; 1:29-62). Potential sources of metal adduct ions can be found throughout a conventional LC system configuration, as shown in FIG. 1. Glass surfaces such as the ones found in reservoir bottles and sample vials can contain trace amounts of alkali metal salts as a byproduct of the manufacturing process used to produce them. Leaching of these trace metal salts can occur in the presence of solvents, acids and bases (Varshneya, Fundamentals of inorganic glasses, Elsevier, 2013). Purity of the solvents used in chromatographic separations can also increase the concentration of salt ions present in an analytical separation. Similarly, the abundance of alkali metal salts in biological samples can also contribute to adduct formation in ESI-MS based analyses. Furthermore, the chromatography system itself can also act as a source of metal adduct ions as alkali metal salts are deposited on high surface area points of contact found throughout the system, such as mixers, filtering frits, and column frits. Therefore, an easy and robust method for reducing the amount of alkali metal salts present in an analytical system and for increasing the sensitivity of detection and/or quantification of a negatively charged analyte, such as an oligonucleotide, is needed.

BRIEF DESCRIPTION OF THE TECHNOLOGY

Accordingly, the present technology provides methods for increasing sensitivity of detection and/or quantification of a negatively charged analyte, such as an oligonucleotide. The methods of the technology reduce the amount of alkali metal salts that may be present in an IP-RPLC and MS analytical system, e.g., anywhere along the fluidic path from the mobile phase reservoir to the detector.

In some embodiments, the present technology provides a method for increasing sensitivity of detection and/or quantification of a negatively charged analyte, the method comprising:

(a) passing an acidic solution through a liquid chromatography-mass spectrometry system comprising an ion-pairing reversed phase liquid chromatography (IP-RPLC) column to remove metal ion adducts;

(b) applying a sample comprising said negatively charged analyte onto the IP-RPLC column and performing chromatographic separation of the sample, followed by mass spectrometry in a negative ion mode, thereby obtaining mass spectrum corresponding to the sample.

In some aspects, the liquid chromatography-mass spectrometry system comprises a mobile phase reservoir and a detector; and the metal ions adsorbed to charged sites in the fluidic path from the mobile phase reservoir to the detector are removed and/or displaced.

In some aspects, the mass spectrum comprises a peak corresponding to the negatively charged analyte; and wherein relative abundance of the peak is increased as compared to a relative abundance of a peak comprised in a mass spectrum obtained by a method that comprises step (b) but not step (a).

In some embodiments, the increase in relative abundance of the peak corresponding to the negatively charged analyte is a measurable increase. In other embodiments, the increase in relative abundance of the peak corresponding to the negatively charged analyte is proportional to the amount of the metal ion adducts removed in step (a).

In some aspects, the sensitivity of detection and/or quantification of the negatively charged analyte is increased at least about 1.1-fold to about 10-fold, e.g., at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold or at least about 10-fold, relative to sensitivity of detection and/or quantification of the negatively charged analyte in a method that comprises step (b) but not step (a). In a specific embodiment, the sensitivity of detection and/or quantification of the negatively charged analyte is increased at least about 2-fold relative to sensitivity of detection and/or quantification of the negatively charged analyte in a method that comprises step (b) but not step (a).

In certain embodiments, the mass spectrum comprises one or more peaks corresponding to the metal ion adducts with relative abundance of less than 10%.

In some aspects, relative abundance of the peak corresponding to the negatively charged analyte in the mass spectrum is greater than 50%. In a further aspect, the relative abundance is greater than 60%, greater than 65%, greater than 70%, greater than 75%, greater than 80%, greater than 85%, greater than 90%, or greater than 95%.

In some embodiments, the acidic solution in step (a) comprises an acid that can produce a sufficient concentration of positive hydrogen ions (H+) in solution that can displace adsorbed metal ions in the fluidic path. In some embodiments, the acid is a weak acid, e.g., formic acid, acetic acid, propionic acid, butyric acid, valeric acid, caprioic acid, lactic acid, malic acid, citric acid, benzoic acid, carbonic acid, trichloroacetic acid, hydrofluoric acid, hydrocyanic acid, oxalic acid, sulfurous acid, hydrogen sulfate ion, phosphoric acid and nitrous acid.

In some aspects, step (a) is carried out for 1 minute, 2 minutes, 3 minutes, 5 minutes, 10 minutes or 15 minutes. In other aspects, step (a) is carried out for less than 1 minute.

In some embodiments, the negatively charged analyte is a nucleic acid or a derivative or analog thereof. In some embodiments, the nucleic acid is an oligonucleotide, e.g., an aptamer or an RNAi. In one embodiment, the oligonucleotide is formivirsen (Vitravene) or pegaptinib (Macugen).

In general, embodiments of the above aspects of the technology include one or more of the following advantages. For example, implementation of a short, low pH reconditioning step results in an effective displacement of trace metal salts non-specifically adsorbed to surfaces in the fluidic path. In some embodiments, the high recovery of spectral abundance using the present methods resulted in a 2-fold or greater increase in MS sensitivity and a significant reduction in spectral complexity, with only a single adduct form observed. Some of the present methods provide the ability to rapidly regenerate adsorption sites with minimal impact on productivity while increasing assay sensitivity afforded by the MS detection with reduced adduct formation. These assay attributes are highly desirable in the analysis of therapeutic oligonucleotides for ensuring product safety, efficacy, and stability.

DETAILED DESCRIPTION OF THE TECHNOLOGY

The present technology provides methods for increasing sensitivity of detection and/or quantification of a negatively charged analyte, e.g., an oligonucleotide, using an analytical system that comprises liquid chromatography and mass spectrometry. The methods comprise passing an acidic solution through the analytical system, i.e., through a fluidic path from the mobile phase reservoir to the detector. The present technology is based on the surprising discovery that incorporating a low pH reconditioning step, i.e., passing an acidic solution through the liquid chromatography-mass spectrometry system, significantly increases relative spectral abundance of a peak corresponding to [M-H]⁻, the deprotonated negatively charged analyte, e.g., an oligonucleotide. The spectral abundance of the [M-H]⁻ ion was recovered, as compared to the spectral abundance of the [M-H]⁻ ion measured in an analytical method that did not employ the low pH reconditioning step.

Figure 1:
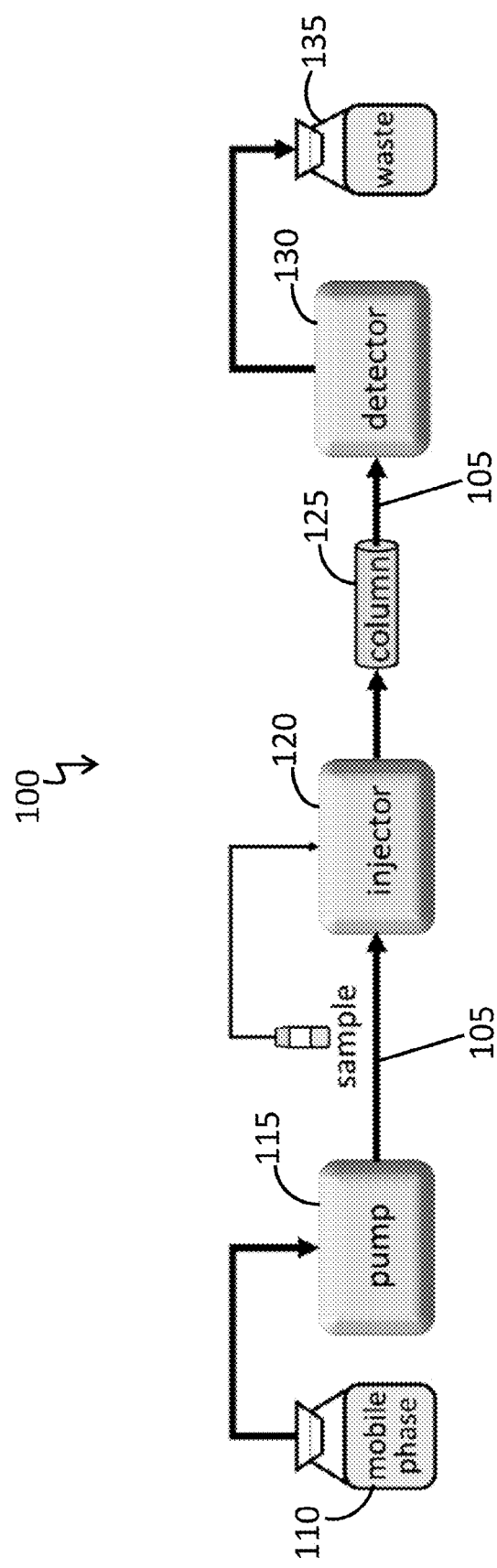
FIG. 1 is an illustration of the basic instrument configuration, including major components found in a basic liquid chromatography used in oligonucleotide separations.

Referring to FIG. 1, shown is an analytical system 100, which can be utilized in carrying out the methods of the present technology. As illustrated in FIG. 1, analytical system 100 includes one or more components connected along a fluidic path 105. In particular, the analytical system 100 includes a mobile phase source or reservoir 110, pump 115, a sample injector 120, a column 125, such as for example, an ion-pairing reversed phase liquid chromatography column, a detector 130, such as, for example, a mass spectrometry detector, and a waste collector 135. The components of the analytical system 100 are in fluidic communication such that they are connected in series along fluidic path 105, with the mobile phase reservoir 110 being the first component in the series (e.g., upstream of the detector 130) and the waste collector 135 being the last component in the series (e.g., downstream of the detector 130). Mobile phase supplied from the mobile phase reservoir 110 is pumped downstream via pump 115 which carries the mobile phase to the sample injector 120 (which introduces a sample into the mobile phase). The mobile phase then carries the sample into the column 125 for a chromatographic separation. The separated sample flows through the mass spectrometer 130 for further separation and detection. The flow leaves the mass spectrometry detector 130 and enters the waste collector 135.

The methods of the technology reduce the amount of alkali metal salts that may be present in an IP-RPLC and MS analytical system, e.g., anywhere along the fluidic path from the mobile phase to the detector.

In some embodiments, the present technology provides a method for increasing sensitivity of detection and/or quantification of a negatively charged analyte, the method comprising:

(a) passing an acidic solution through a liquid chromatography-mass spectrometry system comprising an ion-pairing reversed phase liquid chromatography (IP-RPLC) column to remove metal ion adducts;

(b) applying a sample comprising said negatively charged analyte onto the IP-RPLC column and performing chromatographic separation of the sample, followed by mass spectrometry in a negative ion mode, thereby obtaining mass spectrum corresponding to the sample.

The term "negatively charged analyte", as used herein, refers to any molecule that carries a negative charge. This term encompasses a negatively charged small molecule or a biologic, such as a protein, a peptide, an antibody, a vaccine, a nucleic acid molecule, or a PNA molecule. In some embodiments, the negatively charged analyte is a nucleic acid molecule or a derivative or an analog thereof. The nucleic acid may be an RNA molecule, a DNA molecule, an RNA-DNA hybrid molecule, an aptamer, or an RNAi molecule. In some embodiments, the nucleic acid molecule may be an oligonucleotide, e.g., a DNA oligonucleotide, an RNA oligonucleotide or a DNA-RNA hybrid oligonucleotide.

The term "a derivative of a nucleic acid" or "an analog of a nucleic acid", refers to a nucleic acid molecule that comprises one or more chemical modifications and/or conjugations that are known in the art. Derivatives and/or analogs of a nucleic acid may comprise one or more of the following: a modified backbone, a modified sugars moiety and/or a modified base.

Non-limiting examples of modified nucleic acid backbones include, for example, phosphorothioates, chiral phosphorothioates, phosphorodithioates, phosphotriesters, aminoalkylphosphotriesters, methyl and other alkyl phosphonates, including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'.

Non-limiting examples of modified sugar moieties include, for example, at least one of the following at the 2'-position or the 3' position of the sugar, e.g., ribose or deoxyribose: methoxy ($OCH_3$), aminopropoxy ($2'$-$OCH_2CH_2CH_2NH_2$), OH and F. Nucleic acid molecules with modified sugar moieties may also comprise sugar mimetics such as furan or cyclobutyl moieties in place of the pentofuranosyl sugar.

Non-limiting examples of modified bases include, for example, deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine.

The term "negatively charged analyte" also encompasses any small molecule or a biologic with therapeutic activity, e.g., a therapeutic oligonucleotide. In a specific embodiment, the therapeutic oligonucleotide may be formivirsen (Vitravene) or pegaptinib (Macugen). In some embodiments, the therapeutic oligonucleotide may be an aptamer or an RNAi.

In some embodiments, the methods of the technology comprise passing an acidic solution through a liquid chromatography-mass spectrometry system comprising an ion-pairing reversed phase liquid chromatography (IP-RPLC) column to remove metal ion adducts. The acidic solution comprises an acid that can produce a sufficient concentration of positive hydrogen ions ($H^+$) in solution that can displace adsorbed metal ions in the fluidic path. In some embodiments, to remove metal ion adducts from the liquid chromatography-mass spectrometry system, the acidic solution may be introduced into the system as a mobile phase via a mobile phase source or reservoir. For example, referring to FIG. 1, the acidic solution may be introduced into the analytical system 100 via the mobile phase source or reservoir 110. In some embodiments, the acidic solution introduced into the system as a mobile phase may be used for both removing metal ion adducts from the system and for subsequent chromatographic separation of the negatively charged analyte. In other embodiments, the acidic solution introduced into the system as a mobile phase may only be used for removing metal ion adducts from the system, and is subsequently replaced with a different mobile phase for subsequent chromatographic separation of the negatively charged analyte. Thus, more than one type of mobile phase can be used in analytical system 100. A first mobile phase stored in reservoir 110 can be a wash used prior to flow a sample through the system for separation. In this embodiment, first mobile phase (i.e., wash) comprises an acidic solution. After washing the system 100 with the acidic solution, the first mobile phase in reservoir 110 is replaced with a second mobile phase. The second mobile phase is used to carry a sample (via injector 120) into the column 125 for separation.

Alternatively or additionally, the acidic solution may introduced into the liquid chromatography mass spectrometry system as a part of a sample via a sample injector. For example, referring to FIG. 1, the acidic solution may be introduced into the analytical system 100 via the injector 120.

In some embodiments, the acid comprised in the acidic solution is a weak acid. Non-limiting examples of a weak acid include, e.g., formic acid, acetic acid, propionic acid, butyric acid, valeric acid, caprioic acid, lactic acid, malic acid, citric acid, benzoic acid, carbonic acid, trichloroacetic acid, hydrofluoric acid, hydrocyanic acid, oxalic acid, sulfurous acid, hydrogen sulfate ion, phosphoric acid and nitrous acid.

In some aspects, the liquid chromatography-mass spectrometry system comprises a mobile phase reservoir and a detector; and the metal ions adsorbed to charged sites in the fluidic path from the mobile phase reservoir to the detector are removed and/or displaced. This removal and/or displacement of the metal ions results in a decreased amount of metal adducts and increases the sensitivity of the analysis. In certain embodiments, mass spectrum obtained as a result of carrying out methods of the technology comprises one or more peaks corresponding to metal ion adducts with relative abundance of less than 10%, e.g., less than 9%, less than 8%, less than 7%, less than 6%, less than 5.5%, less than 5%, less than 4.5%, less than 4%, less than 3.5%, less than 3%, less than 2.5%, less than 2%, less than 1.5%, or less than 1%.

In some aspects, the mass spectrum obtained as a result of carrying out methods of the technology comprises a peak corresponding to the negatively charged analyte. In some aspects, the relative abundance of the peak corresponding to the negatively charged analyte is increased, e.g., increased 1.1-fold, 1.5-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold or 10-fold, as compared to a relative abundance of a peak comprised in a mass spectrum obtained by a method that comprises step (b) but not step (a).

In some embodiments, the increase in relative abundance of the peak corresponding to the negatively charged analyte is a measurable increase. The term "measurable increase in relative abundance", refers to any increase in the relative abundance of the peak that may be detected and/or quantified and determined to be significantly different from the earlier measurements. The measurable increase in relative abundance of a peak corresponding to the negatively charged analyte may be, e.g., at increase of 1.1-fold, 1.5-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold or 10-fold, as compared to the earlier measurements.

In other embodiments, the increase in relative abundance of the peak corresponding to the negatively charged analyte is proportional to the amount of the metal ion adducts removed in step (a).

In some aspects, the sensitivity of detection and/or quantification of the negatively charged analyte afforded by the methods of the technology is increased at least 2-fold relative to sensitivity of detection and/or quantification of the negatively charged analyte in a method that comprises step (b) but not step (a). In other aspects, the sensitivity of detection and/or quantification of the negatively charged analyte is increased at least 1.1-fold, 1.5-fold, 2.0-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold or 10-fold, relative to sensitivity of detection and/or quantification of the negatively charged analyte in a method that comprises step (b) but not step (a).

Relative abundance of the peak corresponding to the negatively charged analyte in the mass spectrum is greater than 50%, e.g., greater than 60%, greater than 65%, greater than 70%, greater than 75%, greater than 80%, greater than 85%, greater than 90%, or greater than 95%. In other aspects, relative abundance of the peak corresponding to the negatively charged analyte in the mass spectrum is greater than 10%, e.g., greater than 15%, greater than 20%, greater than 25%, greater than 30%, greater than 35%, greater than 40%, greater than 45% or greater than 50%.

In some embodiments, the acidic solution in step (a) comprises an acid that can produce a sufficient concentration of positive hydrogen ions (H+) in solution that can displace adsorbed metal ions in the fluidic path. In some embodiments, the acid is a weak acid, e.g., formic acid, acetic acid, propionic acid, butyric acid, valeric acid, caprioic acid, lactic acid, malic acid, citric acid, benzoic acid, carbonic acid, trichloroacetic acid, hydrofluoric acid, hydrocyanic acid, oxalic acid, sulfurous acid, hydrogen sulfate ion, phosphoric acid and nitrous acid.

In some aspects, step (a) is carried out for 1 minute, 2 minutes, 3 minutes, 5 minutes, 10 minutes or 15 minutes. In other aspects, step (a) is carried out for less than 1 minute.

EXEMPLIFICATION OF THE TECHNOLOGY

The objective of this study was to systematically evaluate contributing factors in metal adduct formation during analysis of oligonucleotides by IP-RPLC coupled to ESI-MS and to determine new methods to reduce these metal adducts.

Materials and Methods

Triethylamine (P/N 90337, 99.5% purity) and 1,1,1,3,3,3-Hexafluoro-2-propanol manufactured by Aldrich Chemicals (P/N 105228, 99% purity) as well as triethylamine (P/N 65897, 99.5% purity) and 1,1,1,3,3,3-Hexafluoro-2-propanol manufactured by Fluka (P/N 42060, 99.8% purity) were purchased from Sigma Aldrich (St. Louis, Mo.). Mass spectrometry grade solvents (Optima series) and 500 mL low-density polyethylene bottles were purchased from Fisher Scientific (Pittsburgh, Pa.). PolyT oligonucleotide standards and polypropylene 12×32 mm screw neck vials with cap were purchased from Waters (Milford, Mass.). Phosphodiester ssRNA sequences with double thymine overhangs were ordered from Integrated DNA Technology (Coralville, Iowa) and had the following sequences: 5'-UCGUCAAGCGAUUACAAGGTT-3' and the complementary strand 5'-TTCCUUGUAAUCGCUUGACGA-3'. Oligonucleotide samples were prepared at a concentration of 10 pmol/μL. Mass loads on column were kept constant at 50 pmol or 5 μL injections.

Chromatography

A UHPLC system configured with Bio-inert tubing (ACQUITY® H-Class Bio, Waters Technologies Corp.) was used for the study. A tunable UV detector (ACQUITY® TUV, Waters Technologies Corp.) equipped with a 5-mm titanium flow cell was used for optical detection. Single wavelength detection was performed at an Amax of 260 nm with a sampling rate of 2 Hz. An OST BEH™ C18 column (130 Å, 1.7 μm, 2.1 mm×50 mm, Waters Technologies Corp.) was used for all separations at a set temperature of 60° C. Mobile phases (MP) were prepared gravimetrically as MP A: 15 mM TEA, 400 mM Hexafluoroisopropanol (HFIP) in $H_2O$, MP B: 15 mM TEA, 400 mM HFIP in methanol, MP C: $H_2O$, 0.2% FA v/v, MP D: MeOH.

High pH regeneration gradients using MP A and MP B were performed with initial conditions set at 18% MP B. A 4 minute gradient to 20.0% MP B was applied at a flow rate of 0.200 mL/min. The eluent composition was then changed to MP B to 50% and held for 2 minutes to recondition the column. The MP composition was then returned to initial conditions and flowed using isocratic conditions for 4 minutes for a total run time of 10 minutes.

Low pH regeneration gradients using MP A, MP B, MP C, and MP D were performed with initial conditions set at 18% MP B. A 4 minute gradient to 20.0% MP B was applied at a flow rate of 0.200 mL/min. The eluent composition was then changed to MP C and MP D set at 50% each and held for 1 minute to recondition the column. The MP composition was then returned to initial conditions using MP A and MP B and flowed using isocratic conditions for 5 minutes for a total run time of 10 minutes.

MS Settings

A single quadrupole mass spectrometer (ACQUITY® QDa®, Waters Technologies Corp.) was used for MS analysis post TUV detection. MS data was collected throughout the separation as defined in the chromatography section with the flow continuously passing through the MS capillary and the MS polarity mode set to negative. Adjustable instrument settings were set as follows: capillary voltage 0.8 kV, sample cone 20.0 V, source temperature 600° C. An m/z scan range was collected from 410 m/z to 1250 m/z. MS acquisition were processed within the chromatography data system MassLynx® (Waters Technologies Corp.) to assess alkali metal adduct formation using the MaxEnt™ 1 algorithm for deconvolution. High throughput screening MS acquisition data was processed with ProMass® (Novatia) using default parameters.

Results

Example 1. Borosilicate Glassware

Efforts to minimize alkali metal salt adduct formation were taken prior to beginning the current study. As a potential point source of metal salt ions, solvent glassware and sample vials were replaced with plastic alternatives constructed from polyethylene and polypropylene, respectively. To this end, solvent bottles were soaked overnight in 60% isopropyl alcohol to remove leachable impurities such as residual monomer and hardening agents (Jenke D., *Journal of Pharmaceutical Sciences* 2007; 96:2566-81). Polypropylene sample vials were used as received. To establish a baseline response, the LC system was purged with a 30% phosphoric acid solution that was flowed through the system as a mobile phase to wash out residual alkali metal salts in the fluidic path, immediately followed by a rinse with MS-grade water. After cleaning, the LC system was prepared for oligonucleotide analysis using an IP-RPLC mobile phase prepared with TEA and HFIP. A 10 minute high throughput method was used to provide statistical figures of merit and evaluate adduct formation over an efficient time frame.

Using an injection series that incorporates a full 48-well sample plate, ssRNA upper strand samples were prepared in MS-grade water and transferred to polypropylene vials across the 48 wells. The ssRNA lower strand was loaded in every 7th vial position as a negative control. A single quadrupole mass detector was configured in a serial configuration post optical detection to evaluate alkali metal salt adducts in deconvoluted spectrum. Spectral abundance of the ssRNA upper strand [M-H]⁻ species (parent peak) as percent total peak intensity, including adduct forms, was plotted from the deconvoluted MS data over the course of the injection series. The resulting bar graph is shown in FIG.

Figure 2:
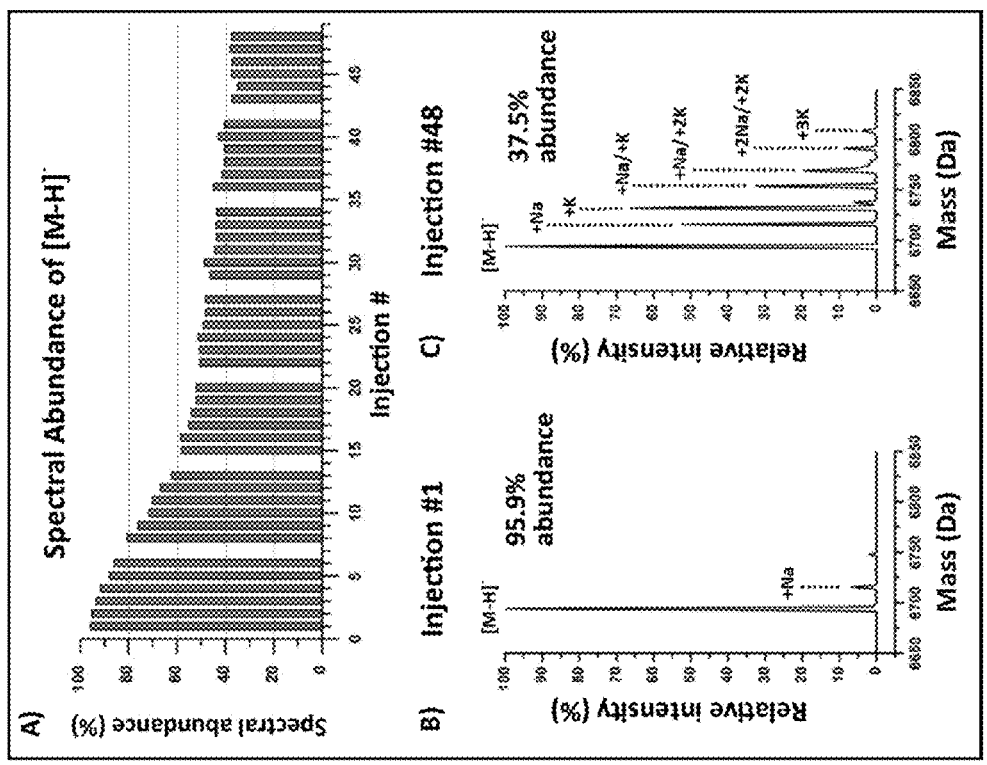
FIG. 2 demonstrates the recovery of peak intensity of the [M-H]− peak in a clean LC system as compared to the contaminated LC system. Panel A is a spectral abundance trending plot showing % spectral abundance over the course of an 8 hour injection series. Deconvoluted peak intensity of the [M-H]− species of the ssRNA upper strand as % total intensity was used to determine spectral abundance over the course of an 8 hour injection series. Panel B is a deconvoluted MS spectrum obtained for injection #1 that was used as a baseline reference. The [M-H]− peak was observed in a clean LC system at 95.9% spectral abundance, as compared to its +Na adduct form (4.1%). Panel C is a decovoluted spectrum obtained for injection #48, indicating that over 65.7% of the spectral abundance of the ssRNA upper strand is in adduct form representing a contaminated LC system.

2, Panel A. Injection #1, shown in FIG. 2, Panel B, was used as a baseline reference for adduct evaluation. Sodium and potassium adducts were observed to have a relative intensity below 6% and 1%, respectively, in the deconvoluted spectrum of injection #1 of the ssRNA upper strand. Considering the ubiquitous nature of alkali metal salts in LC based methods, it is not unexpected that trace-level impurities will still be present despite running the assay immediately following the system cleaning protocol, therefore these levels were considered acceptable. The significant decrease in spectral abundance from 95.9% to 34.3% abundance over the course of the injection series (FIG. 2, Panel A) was unexpected. As shown in FIG. 2, Panel C, the peaks in the deconvoluted spectra were determined to correspond to single and multiple adducts of sodium and potassium. The data indicates that the borosilicate glassware is not a significant source of alkali metal salts because the injection series was performed with a newly prepared set of TEA/HFIP buffers with plastic substitutes in lieu of borosilicate glassware.

The data presented in FIG. 2, Panel A demonstrates that the cleaning protocol involving a purge with a 30% phosphoric acid solution is sufficient to remove residual alkali metal salts from the system flow path. This is evidenced by a low degree of adduct formation in injection #1 performed a short time after the cleaning protocol was completed. Additionally, the significant increase in adduct formation over multiple injections in a system that involves plastic alternatives to solvent glassware and glass vials indicates that borosilicate glassware is not a contributing factor to alkali metal salts in the studies experimental design.

Example 2. Sample Purity

Figure 3:
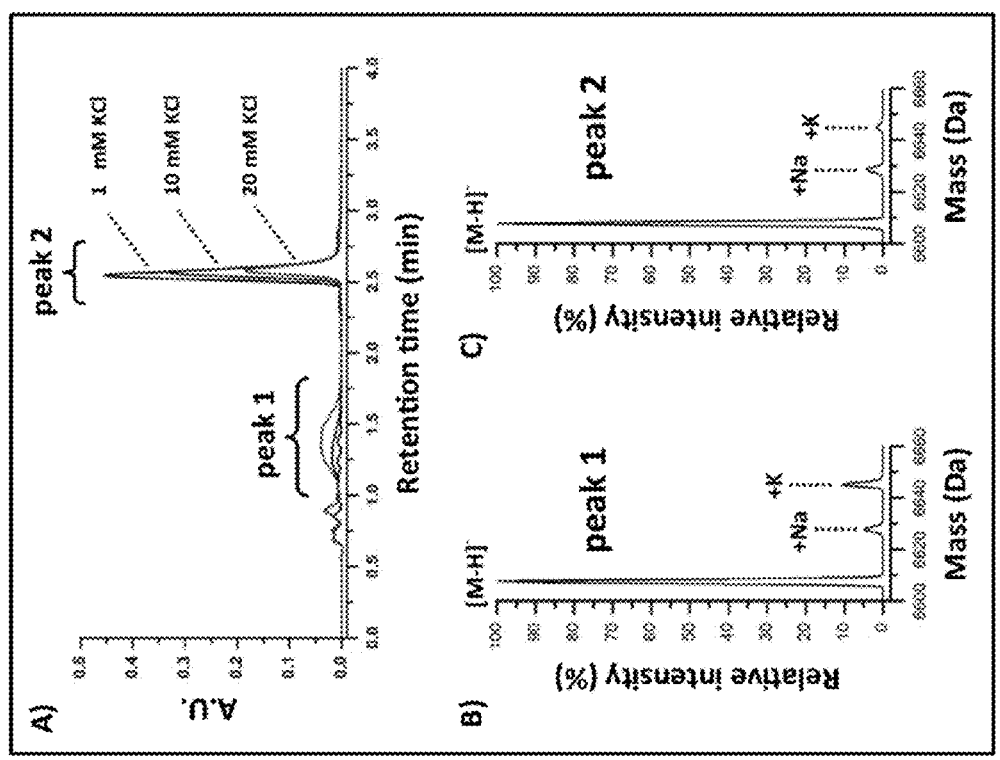
FIG. 3 shows LC and MS spectra for samples at various salt concentrations. Panel A is a UV chromatogram of the ssRNA lower strand prepared in 1 mM (black trace), 10 mM (blue trace), and 20 mM KCl (green trace). Panel B is a deconvoluted MS spectrum of peak 1 obtained for a sample containing 20 mM KCl. The spectrum shows that relative intensities of the +Na and +K adducts are, respectively, 4.6% and 10.6%. Panel C is a deconvoluted MS spectrum of a later eluting peak 2 obtained for a sample containing 20 mM KCl. The spectrum shows that relative intensities of the +Na and +K adducts are, respectively, 4.1% and 1.8%.

By a process of elimination, the sample, the column, the injector, and the solvents may be potential point sources of alkali metal salts as shown in FIG. 1. Using the same system configuration as in Example 1 (with polyethylene mobile phase bottle and polypropylene sample vials), the samples used in the study were examined as a point source for alkali metal salts. Prior to sample evaluation, the system's fluidic path was cleaned as before to remove residual metal salts. Sodium adducts were observed with a relative intensity of 5% using the ssRNA lower strand sample prepared in water as a control to evaluate system cleanliness (data not shown). Potassium adducts were not observed in the control sample. A 100 mM KCl solution was used to prepare test samples of the ssRNA lower strand with final salt concentrations ranging from 0.5 mM KCl up to 50 mM KCl. Injection volume was adjusted to maintain a 50 pmol on-column mass load using the same 10 minute method as before. Chromatogram overlays of samples prepared in 1 mM KCl, 10 mM KCl, and 20 mM KCl are shown in FIG. 3, Panel A. Two peaks of interest were observed to change with increasing KCl concentration. Peak 1, centered around 1.3 minutes, is broad and increases in intensity with increasing KCl concentration. A loss of resolution with failed sequence peaks (N-x) from 0.5 minutes to 1.5 minutes was also observed in the same chromatographic region. Peak 2, centered around 2.6 minutes, decreases in intensity with increasing KCl concentration and was observed to show a modest increase in retention time with increasing KCl concentration. The acquired MS data was investigated using the 20 mM KCl sample for additional insight into the behavior observed in the UV chromatograms.

MS spectra were combined using an equal number of scans from 1.0 to 2.0 minutes and 2.4 to 3.4 minutes for peak 1 and peak 2, respectively. As shown in FIG. 3, Panel B, deconvolution of peak 1 spectrum indicates that the broad peak corresponds predominantly to the ssRNA lower strand, with sodium and potassium adducts observed with relative intensities of 4.6% and 10.6%, respectively. As shown in FIG. 3, Panel C, deconvolution of peak 2 spectrum indicates that this peak also corresponds to the ssRNA lower strand, but with sodium and potassium adducts observed with lower relative intensities of 4.1% and 1.8%, respectively. The retention time shift and relative intensity changes observed in the UV chromatogram combined with the decreasing adduct intensity from the MS data indicate that samples are being simultaneously desalted as they are electrostatically attracted to the IP reagent adsorbed on the column bonded phase (Gilar M, Bouvier ESP, *Journal of Chromatography A* 2000; 890:167-77).

To further investigate this, a sample prepared in 50 mM KCl was analyzed. A 30 minute separation gradient using a lower initial organic composition (MP B 5%) was used to improve IP efficiency. Peak splitting was observed in the chromatographic profile of the ssRNA lower strand, and the MS spectrum indicated presence of a sodium adduct with a relative intensity of 7.2% (data not shown). Interestingly, potassium adducts were not observed in the deconvoluted MS data. This further confirms that oligonucleotides, when used in this experimental design, are effectively retained and desalted prior to MS analysis. Collectively, this data demonstrates that the samples which were desalted post synthesis by the manufacturer are not a significant contributing source of alkali metal salt adducts in oligonucleotide separation.

Example 3. Column Salt Tolerance

Figure 4:
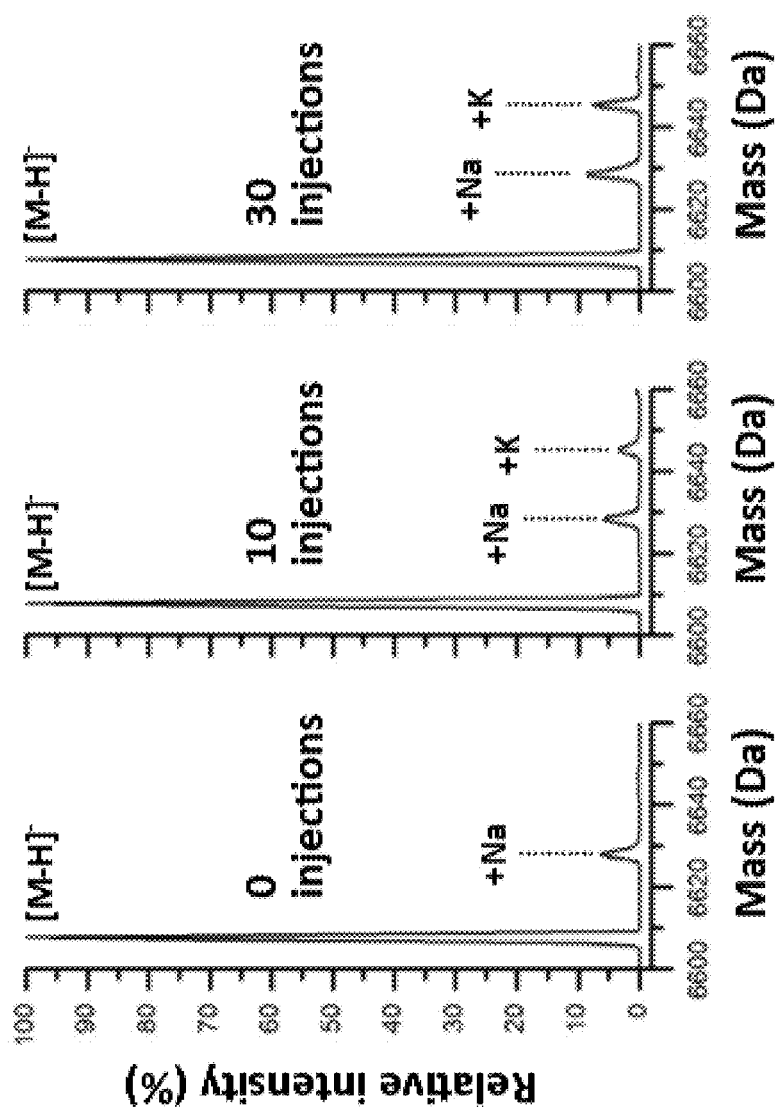
FIG. 4 shows three deconvoluted MS spectra of the ssRNA lower strand after 0, 10 and 30 injections of a water blank containing 100 mM KCl. Relative intensity of the sodium adduct is 6.3%, 5.8%, and 8.5% for the 0, 10, and 30 injection runs, respectively. The potassium adduct is not observable in the 0 injection run, but increases proportionally in the 10 and 30 injection runs with relative intensity of 3.3% and 7.8%, respectively.

The data obtained in Example 2 indicated that the column was effectively desalting heavily salted samples. The experiments in Example 2 were conducted with a small sample set size at modest KCl concentration and did not characterize column tolerance to repeated salt exposure. To evaluate column tolerance to metal salt exposure, an isocratic method was designed with the MP composition of B set to 19% to allow the ssRNA lower strand to elute within 1.5 minutes. Performing the assay using isocratic conditions minimizes the impact the column reconditioning step may have on reducing adduct formation. The system was cleaned of residual alkali metal salts prior to the experiment. Using a water blank containing 100 mM KCl, 10 μL injections were performed with the isocratic method using a 1 minute run time. The ssRNA lower strand was prepared in water and injected after 0, 10, and 30 injections of the 100 mM KCl water blank. The samples were analyzed using the same isocratic method with a 4 minute run time to allow sufficient time for the sample to elute. FIG. 4 shows the resulting deconvoluted MS spectra of the ssRNA lower strand obtained after 0, 10, and 30 injections of the 100 mM KCl water blank.

As demonstrated by the deconvoluted MS spectra in FIG. 4, adduct formation and intensity were observed to increase with multiple injections of the 100 mM KCl water blank. The baseline reference acquired prior to the salt blank injections (0 injections), indicated that sodium adducts were present at a relative peak intensity of 6.3%, which was consistent with the previous results. The sodium adducts were observed to show a modest increase in relative peak intensity up to 8.5% after the 30th injection of the 100 mM KCl salt blank. Similar behavior was also observed for the potassium adducts, which increased proportionally in relative intensity from 3.3% to 7.8% following 10 and 30 KCl injections, respectively. The observation of metal adduct formation following injections of KCl blanks from this experiment suggests there is a degree of non-specific adsorption of alkali metal adducts occurring between the time of injection and detection, possibly in the column itself.

This data was compared to the 4th injection of the trending data shown in FIG. 2, Panel A (spectral abundance 91.7%). The $4^{th}$ injection of FIG. 2, Panel A spatially represents the same amount of experimental time or column volume (CV) of mobile phase passed over the column (46 CV). In the $4^{th}$ injection, potassium adducts were observed at trace levels (<1%) in the deconvoluted MS spectrum, with sodium adducts accounting for the remaining 8.3% of the spectral abundance. Interestingly, in the 30th injection of the trending data shown in FIG. 2, Panel A, which represents the same number of injections as the current experiment, but an 8-fold increase in column volumes (347 CV) of mobile phase passed over the column, the spectral abundance was reduced to 50.6%, with multiple adducts of sodium and potassium observed. The current experiment repeatedly exposed the fluidic path between the injector and detector to an artificially elevated level of KCl in less CVs as compared to the experiment described in Example 1, but resulted in only a marginal increase in adduct formation. This suggests that the exposed fluidic path, including the column, is resistant to non-specific adsorption of alkali metal salts and is not the major contributor to adduct formation in oligonucleotide analyses in the current experimental design.

Example 4. Mobile Phase

It was observed in the previous experiment that a marginal amount of non-specific adsorption of alkali metal salts occurs in the fluidic path between the injector and detector, and that it is not a significant source of alkali metal adducts in oligonucleotide analyses. Furthermore, the number of CVs passed through the fluidic path was observed to have some influence on the formation of metal adducts in oligonucleotide separations. These observations imply that the mobile phase itself may contribute to metal adduct formation over time. To further investigate this phenomena, the 10 minute method previously used for the borosilicate analysis was modified in order to extend the reconditioning step at the end of the gradient to systematically increase the number of CVs the fluidic path is exposed to at initial mobile phase conditions. The system was cleaned of residual alkali metal salts prior to each run in the experiment. For consistency with the borosilicate experiment, the ssRNA upper strand was used for this experiment and prepared at the same concentration as before in MS grade water.

Figure 5:
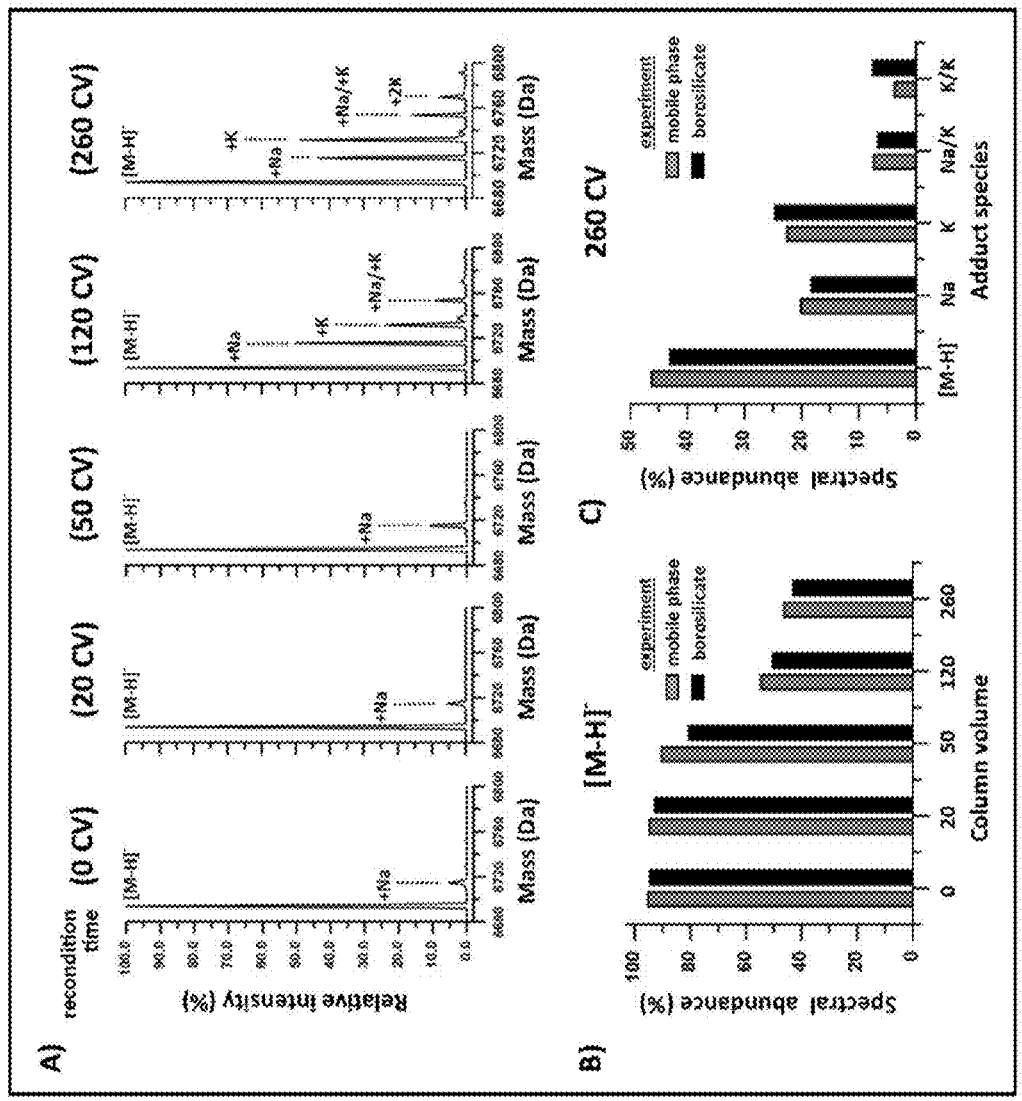
FIG. 5 shows deconvoluted MS spectra and bar graphs demonstrating the effect of mobile phase purity on metal adduct formation. Panel A is a deconvoluted MS spectrum of the ssRNA upper strand after running at initial conditions over the time required for 0, 20, 50, 120, and 260 column volumes. Panel B is a bar graph showing spectral abundances for the [M-H]⁻ peak at equivalent column volumes for the mobile phase (gray bars) and borosilicate (black bars) experimental data set. Panel C is a bar graph showing spectral abundance adduct distribution profile for the mobile phase (gray bars) and borosilicate (black bars) experiments for the 260 CV data set.

As shown in FIG. 5, Panel A, adduct formation increased with CVs that passed through the system. Comparing the results of the 50 CVs experiment (FIG. 5, Panel A) with the 30 injection experiment shown in FIG. 4 (corresponding to 39 CVs of mobile phase passed through the system), it is observed that the sodium adduct exhibits the same trending behavior (10.8% vs. 8.5%). This observation further demonstrates that the mobile phase is a contributing factor to adduct formation.

The current results were compared with the results of the borosilicate experiments described in Example 1 and shown in FIG. 2, Panel A. The chromatographic runs conducted for the borosilicate experiment were within 10 CVs of the current experiment. As shown in FIG. 5, Panel B, the spectral abundance of the [M-H]⁻ peak in the current mobile phase experiment exhibited nearly identical trending behavior as the spectral abundance of the [M-H]⁻ peak in the borosilicate experiments. The 260 CV data set shown in FIG. 5, Panel C demonstrates that there is an almost identical distribution profile of observed adduct species in the experimental data sets. The good agreement in adduct distribution and intensity in the current experiment and the borosilicate experiment indicates that alkali metal impurities present in the mobile phase are the main contributing factor to adduct formation in oligonucleotide separations. The gradual increase in adduct abundance over time as observed in this example and in Example 1 suggests that the impurities are present at a trace level either in the solvent used in the mobile phase preparation or in the IP reagents themselves.

Figure 6:
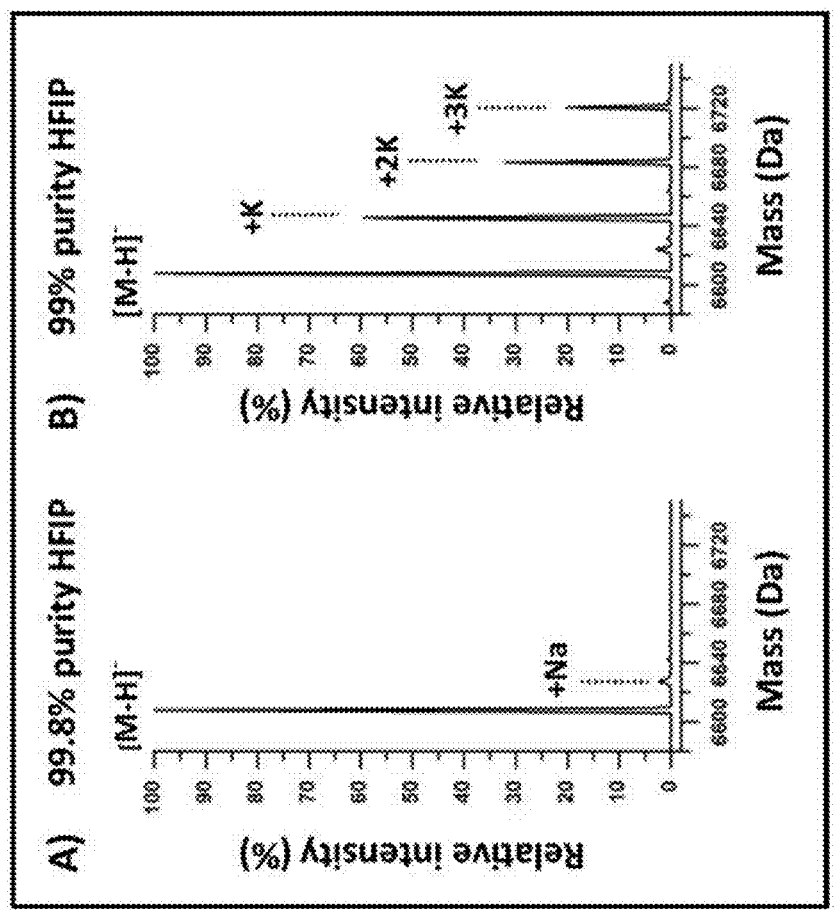
FIG. 6 is a series of decovoluated MS spectra of the initial separation of a ssRNA sample after removal of residual alkali metal salts using 99.8% pure HFIP (Panel A) and 99% pure HFIP (Panel B). Sodium adducts are observed to have similar relative amounts in both the 99.8% purity and 99% purity IP reagents, whereas significant potassium adduct(s) are observed in the initial injection using the 99% purity IP reagent.

To elucidate the source of contamination, HFIP at different purities 99% purity vs. 99.8% purity) was assayed using the 10 minute high throughput method. As before, the system was cleaned prior to each analysis to remove residual alkali metal salts. As shown in FIG. 6, Panel A, HFIP at the 99.8% purity which was used for the previous experiments and is rated for LC-MS use, resulted in a deconvoluted spectrum of the ssRNA with minimal adduct formation. The relative intensity of the sodium adduct was less than 5%, which was consistent with the results of previous experiments. In contrast, as shown in FIG. 6, Panel B, HFIP at the 99% purity resulted in single, double, and triple adducts of potassium. This indicates that a significant amount of potassium is present in the less pure HFIP. System contamination was ruled out as a possibility because the sodium adduct was present at a relative intensity of below 5%, which was consistent with the results for HFIP at the 99.8%, as well as with the previous baseline references.

TEA from two different manufactures rated with the same purity (≥99.5%) was also investigated with similar methodology using the 99.8% MS grade HFIP as a buffer. The results of initial runs showed a single sodium adduct at relative intensity of less than 5%, consistent with the results of previous baseline experiments indicating the TEA was not a significant source of metal adduct ions. Combined, the results demonstrate that the contaminants present in the IP reagents, specifically, HFIP, are responsible for adduct formation in oligonucleotide separations in the current study. With the source of alkali metal adducts identified, a mitigation strategy can be developed to reduce instrument contributions to metal adducts in oligonucleotide separations.

Example 5. Method for Reducing Adduct Formation

The experimental data presented in Examples 1-4 offers several insights into alkali metal salt adduct formation in oligonucleotide separations. Through the process of elimination it was determined in Examples 1-4 that impurities present at trace levels in the mobile phase act as a point-source of alkali metal salts. Trending data shown in the borosilicate experiments (FIG. 2, Panel A) indicates that adduct formation occurs gradually and appears to approach steady-state. This demonstrates that non-specific adsorption sites exist in the fluidic path and exhibit affinity towards positively charged ions, such as sodium and potassium ions, based on the Hoffmeister series. The adsorption process is most likely based on an equilibrium mechanism where the rate of adsorption/desorption of metal ions to the fluidic path surface reach a steady state. In a newly cleaned system this would manifest itself as an increase in adduct formation that plateaus over time, as available ions in solution increase and are electrostatically attracted to the polyanionic phosphodiester backbone in the oligonucleotide. This model is supported by the trending data shown in FIG. 2, Panel A as well as by the data shown in FIG. 2, Panel C and FIG. 5, Panel C. The spectral abundance of the single potassium adduct species is higher than the spectral abundance of the single sodium adduct species because potassium ions exhibit higher affinity to the negatively charged sites than sodium ions. The ubiquitous presence of sodium adducts in the separation, specifically, the initial separations, may indicate higher levels of trace impurities in the starting material or the initial displacement from adsorption sites by potassium ions.

Additional evidence that the adsorption mechanism is electrostatically driven is based on the Hoffmeister series as seen in FIG. 5, Panel B. The experimental data obtain in the mobile phase experiment represents 1 injection performed after running a set number of CVs with the reconditioning step performed once at an organic composition of 50%. In contrast, the data set obtained in the borosilicate experiment, which represents a similar number of CVs, was obtained after multiple injections using the same reconditioning step of 50% organic. However, the spectral abundances in the borosilicate data are only marginally lower, despite the system being exposed to higher concentrations of organic solvent with higher frequency. This suggests that the reconditioning step performed with higher organic composition (50% B) has negligible impact on reducing adduct formation over time. Interestingly though, conventional methods do not incorporate methods to displace or desorb non-specifically adsorbed cations on surfaces along the fluidic path.

Current practices in oligonucleotide separations often involve the use of binary pump systems with MP A prepared in water and containing an IP reagent either buffered in HFIP or titrated to neutral or slightly basic pH using acid. MP B is often prepared by diluting MP A in an organic solvent, such as methanol or acetonitrile, with no pH adjustment. The non-specific adsorption observed in this study, which exhibits behavior analogous to the behavior of a cation exchange surface, requires exposure to solutions that have low pH (are acidic) or contain high concentration of salt to regenerate adsorption sites. Neither acid, nor salt is present in conventionally prepared mobile phases for oligonucleotide separations using LC-MS. This idea is supported by the experimental evidence demonstrating that a baseline performance spectrum (minimal adducts) may be obtained by using a cleaning protocol with phosphoric acid. This knowledge combined with the experimental evidence suggests a method that incorporates a low pH mobile phase can be used to regenerate non-specific adsorption sites and maintain MS compatibility.

Figure 7:
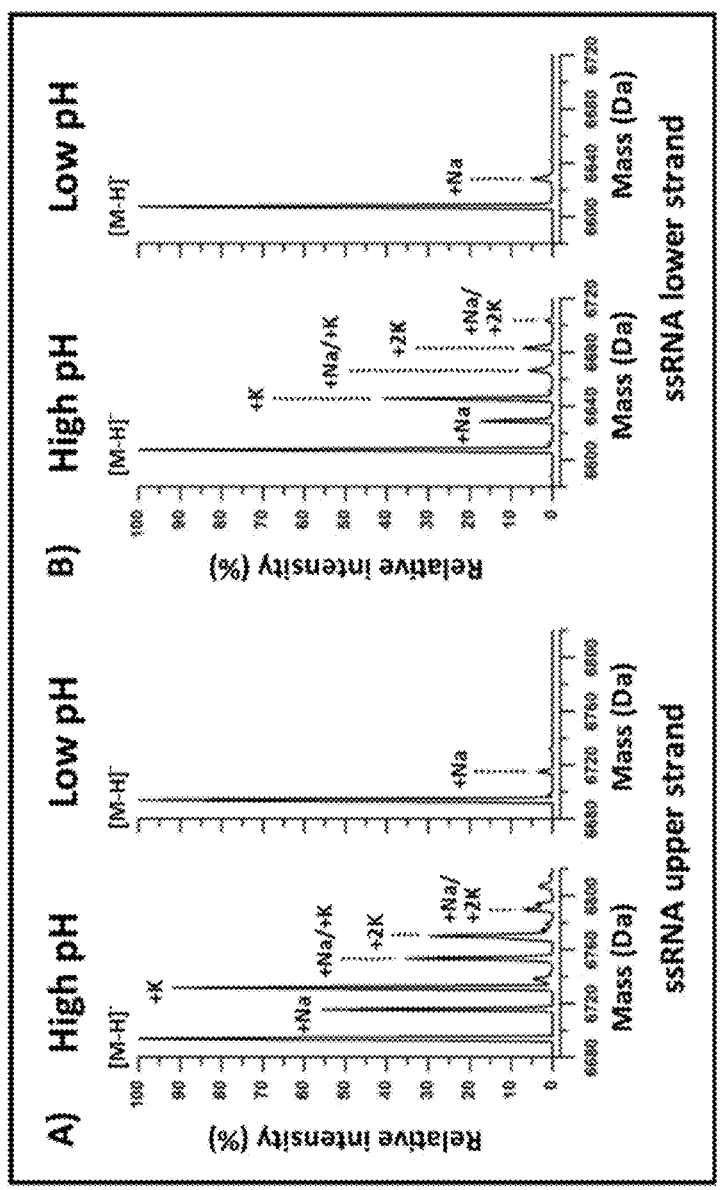
FIG. 7 is a series of deconvoluted MS spectra showing the effect of reconditioning at high pH and low pH. An analytical method that incorporated a low pH reconditioning step was compared to an analytical method that incorporated the conventional high pH reconditioning step for the ssRNA upper strand (Panel A) and ssRNA lower strand (Panel B). Adduct formation was reduced to a single adduct of sodium at 3.5% for ssRNA upper strand and 5.0% ssRNA lower strand.

To test this theory MP C was prepared as 0.2% formic acid in water (MS-grade) and MP D was prepared as neat methanol (MS-grade). The 10 minute method from the borosilicate experiment was used, except that the mobile phase composition was changed to 50% MP C and 50% MP D for 1 minute preceding the separation gradient and then returned to the initial method conditions for column reconditioning. To increase salt contamination levels, the mobile phases were passed through the system using isocratic conditions and the performance was evaluated periodically using the high pH reconditioning method (borosilicate experiment) which does not use MP C or MP D. Deconvoluted MS spectra for the ssRNA upper and lower strands analyzed using the contaminated system (high pH) are shown in the left spectrum of FIG. 7, Panel A (upper strand) and the left spectrum of FIG. 7, Panel B (lower strand).

With the metal salt contamination confirmed, a water blank using the low pH reconditioning method was performed to regenerate the fluidic path surface by displacing non-specifically adsorbed cations. After surface regeneration, the ssRNA samples were separated using the low pH reconditioning method as shown in the right spectrum of FIG. 7, Panel A (upper strand) and the right spectrum of FIG. 7, Panel B (lower strand). Adducts formation was reduced to a single adduct of sodium at 3.5% and 5.0% relative intensity for the ssRNA upper strand and ssRNA lower strand, respectively.

Figure 8:
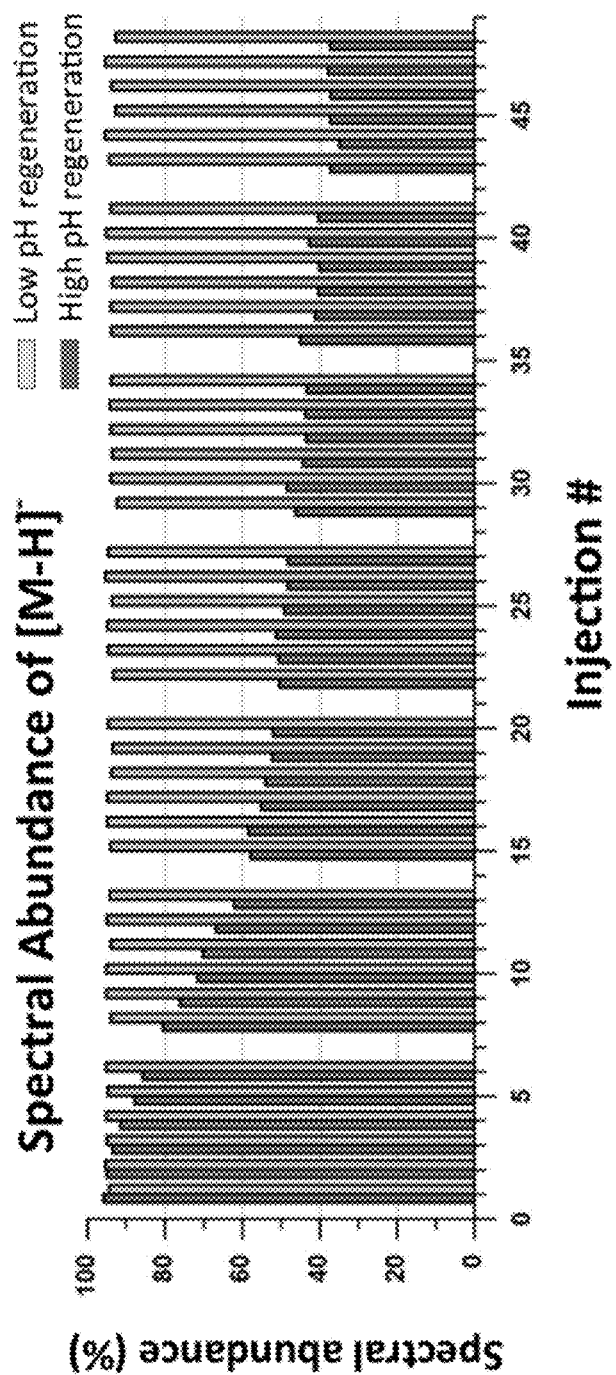
FIG. 8 is a spectral abundance trending plot comparing spectral abundance of the [M-H]- species after low and high pH analytical system reconditioning. Spectral abundance for the [M-H]⁻ species was maintained above 92.5% with a mean value of 94.5% when the low pH reconditioning step was used. This is compared to a 60.9% drop in spectral abundance from 95.9% to 35.0% when high pH reconditioning step was used.

The long-term effectiveness of the low pH reconditioning method for reducing alkali metal salt adducts in oligonucleotide separation was evaluated using the same experimental design as the borosilicate experiments described in Example 1. The low pH reconditioning method was used in lieu of the high pH reconditioning method as described in Example 1, and the results are shown in FIG. 8. Specifically, FIG. 8 shows that when the low pH reconditioning step was used, the spectral abundance for the $[M-H]^-$ species was maintained above 92.5% with a mean value of 94.5%. This compares favorably to the high pH reconditioning method across an 8 hour injection series that results in a 60.9% drop in spectral abundance from 95.9% to 35.0%. These results demonstrate the low pH reconditioning method effectively and consistently displaces non-specifically adsorbed cations on surfaces throughout the LC fluidic path over multiple runs using an MS compatible acid with minimal impact on productivity.

DISCUSSION

IP-RPLC has become a prevalent technique used for the analysis of synthetic oligonucleotides, in part due to the selectivity it offers, as well as its ability to incorporate MS friendly reagents and buffers (Apffel et al., *Analytical Chemistry* 1997; 69:1320-5; Apffel et al., *Journal of Chromatography A* 1997; 777:3-21). Accurate mass determination afforded by MS detection offers an efficient means for characterizing challenging base modifications and improved productivity in synthetic therapeutic oligonucleotide workflows. MS-based methods have also been widely incorporated into assays that require high sensitivity, such as determination of toxicological profiles and metabolite profiles associated with synthetic oligonucleotides. (Waters et al., *Journal of Clinical Oncology* 2000; 18:1812-23; Zhang et al., *Analytical Chemistry* 2007; 79:3416-24). A common challenge in ESI-MS based methods encountered in oligonucleotide separations is their propensity to formation of alkali metal adducts due to the intrinsic electrostatic attraction of metal cations with the polyanionic backbone of oligonucleotides (Apffel et al., *Analytical Chemistry* 1997; 69:1320-5; Zhang et al., *Analytical Chemistry* 2007; 79:3416-24). This problem is accentuated by the fact that IP-RPLC/MS based methods generally operate the MS instrument in negative mode requiring buffers to be maintained in neutral to basic pH conditions. Trace levels of alkali metal salts present as impurities are generally not a concern in routine UV based analyses, but can significantly impact spectral quality in sensitive ESI-MS analyses. Accordingly, localization of the alkali metal salt impurities and mitigation of their effect are necessary to develop successful methods that are robust and efficient.

Current strategies to mitigate metal adduct formation have spanned a diverse set of offline and online approaches. These strategies involve sample preparation, including desalting procedures that incorporate hydrophobic or ion-exchange resins; the use of molecular weight cutoff filters; and solid phase extraction techniques (Gilar et al., *Journal of Chromatography A* 2000; 890:167-77; Ragas et al., *Analyst* 2000; 125:575-81; Jiang et al., *Analytical Biochemistry* 2003; 316:50-7). Alternative approaches aimed at reducing complicated sample preparation procedures include the use of additives such as metal chelators, including CDTA and EDTA, that act as cation scavengers or the use of bases, such as piperidine and TEA, that suppress adduct formation via displacement (Gong and McCullagh, *Rapid Communications in Mass Spectrometry* 2014; 28:339-50; Greig and Griffey, *Rapid Communications in Mass Spectrometry* 1995; 9:97-102).

These approaches, while effective in reducing metal adduct formation, do not address contribution of the instrument to metal salt adducts formation, a challenging task considering the ubiquitous nature of alkali metal salts in LC separations (Keller et al., *Analytica Chimica Acta* 2008; 627:71-81; Ende and Spiteller, *Mass Spectrometry Reviews* 1982; 1:29-62). Potential sources of metal adduct ions can be found throughout a conventional LC system configuration. Alkali metal oxides used in the manufacturing process of laboratory glassware, such as borosilicate glassware, can leach into solvents over time in the presence of acids, bases and organic solvents (Varshneya, *Fundamentals of inorganic glasses*, Elsevier, 2013). Similarly, metal surfaces throughout the fluidic path can potentially leach metal ions via corrosion that occurs when the metal surfaces are exposed to acids and bases commonly used in LC separations. Alternatively, the impurities present in the solvents and reagents can also contribute to adduct formation in LC/ESI-MS based separations. The current study systematically evaluated common components in LC/ESI-MS configurations used in oligonucleotide analysis to provide insight into the contribution of instrumentation to formation of metal adducts and methods for reducing metal adduct formation.

The impurities present in the IP reagents used in this study were identified as the main contributing factor of metal adduct formation in oligonucleotide separations. MS-grade reagents demonstrated the least amount of adduct formation in the current study, a finding not entirely unexpected when sensitive MS-based detection methods are used. Interestingly, adduct intensity and abundance were observed to increase over time despite precautions such as preparing solvents immediately prior to analysis using dedicated preparation glassware, as well as incorporating plastic based alternatives in the LC configuration. These observations combined with the fact the LC system could routinely be brought back to baseline performance with minimal adducts using a low pH cleaning protocol indicated that non-specific adsorption sites located throughout the fluidic path perpetuate adduct formation in oligonucleotide analyses.

Without to be wishing to be bound by a specific theory, it is believed that the adsorption process is an equilibrium mechanism where the rate of adsorption/desorption of metal ions onto/from the fluidic path surface reaches a steady state. This is manifested in the increase of adduct formation that plateaus over time. Perpetuation of adduct formation is due to the fact the adsorption process, which appears to be electrostatically driven, requires low pH in order to displace adsorbed metal ions. These conditions are not typically encountered in IP-RPLC/MS separation of oligonucleotides. Initial findings using lower grade IP reagents demonstrated a significant amount of adduct formation in initial runs and suggested that the non-specific adsorption sites are finite and can be saturated. Despite being present in finite numbers, non-specific adsorption sites in the fluidic path of the current study contributed to over a 60% loss of spectral abundance of the $[M-H]^-$ species due to alkali metal adducts. The recovery of spectral abundance is critical to developing efficient methods that are quantitative and robust.

The collective findings of the current study demonstrated that incorporation of a low pH reconditioning step in the methodology was sufficient to recover a significant amount of spectral abundance of oligonucleotides being analyzed using IP-RPLC/MS based techniques. The high recovery of spectral abundance using the present method resulted in a 2-fold increase in MS sensitivity and a significant reduction in spectral complexity, with only a single adduct form observed. Spectral abundance for the $[M-H]^-$ species was maintained above 92.5% with a mean value of 94.5% and R.S.D. of 0.8% using the low pH reconditioning step across an 8 hour injection series. This represented over a 20-fold improvement in standard deviation when compared to a more traditional method that did not incorporate a low pH reconditioning step, which resulted in a 60.9% drop in spectral abundance from 95.9% to 35.0% using an identical time course study.

The current study demonstrates that presence of trace alkali metal salts can significantly diminish spectral quality in IP-RPLC/MS based analyses of oligonucleotides. The intrinsic electrostatic attraction of metal cations to the polyanionic backbone of oligonucleotides, combined with method conditions that favor adduct formation, make MS based methods of oligonucleotide analysis challenging. The current study elucidates instrument contributions to the formation of metal salt adducts and provides a method for their reduction. Implementation of a short, low pH reconditioning step results in an effective displacement of trace metal salts non-specifically adsorbed to surfaces in the fluidic path. The present method provides the ability to rapidly regenerate adsorption sites with minimal impact on productivity while retaining assay sensitivity afforded by the MS detection with reduced adduct formation. These assay attributes are highly desirable in the analysis of therapeutic oligonucleotides for ensuring product safety, efficacy, and stability.

What is claimed is:

1. A method for increasing sensitivity of detection and/or quantification of a negatively charged analyte, the method comprising:
   (a) passing an acidic solution through a liquid chromatography-mass spectrometry system comprising an ion-pairing reversed phase liquid chromatography (IP-RPLC) column to remove metal ion adducts;
   (b) applying a sample comprising said negatively charged analyte onto said IP-RPLC column and performing chromatographic separation of said sample, followed by mass spectrometry in a negative ion mode, thereby obtaining mass spectrum corresponding to said sample.

2. The method of claim 1, wherein said liquid chromatography-mass spectrometry system comprises a mobile phase reservoir and a detector; and
   wherein metal ions adsorbed to charged sites in the fluidic path from the mobile phase reservoir to the detector are removed and/or displaced.

3. The method of claim 1, wherein said mass spectrum comprises a peak corresponding to said negatively charged analyte; and
   wherein relative abundance of said peak is increased as compared to a relative abundance of a peak comprised in a mass spectrum obtained by a method that comprises step (b) but not step (a).

4. The method of claim 3, wherein said increase in relative abundance of said peak corresponding to the negatively charged analyte is a measurable increase.

5. The method of claim 3, wherein said increase in relative abundance of said peak corresponding to the negatively charged analyte is proportional to the amount of said metal ion adducts removed in step (a).

6. The method of claim 3, wherein said sensitivity of detection and/or quantification of said negatively charged analyte is increased at least about 1.1-fold to about 10-fold relative to sensitivity of detection and/or quantification of said negatively charged analyte in a method that comprises step (b) but not step (a).

7. The method of claim 6, wherein said sensitivity of detection and/or quantification of said negatively charged analyte is increased at least about 2-fold relative to sensitivity of detection and/or quantification of said negatively charged analyte in a method that comprises step (b) but not step (a).

8. The method of claim 1, wherein said mass spectrum comprises one or more peaks corresponding to said metal ion adducts with relative abundance of less than 10%.

9. The method of claim 3, wherein relative abundance of the peak corresponding to said negatively charged analyte in said mass spectrum is greater than 50%.

10. The method of claim 9, wherein said relative abundance is greater than 60%, greater than 65%, greater than 70%, greater than 75%, greater than 80%, greater than 85%, greater than 90%, or greater than 95%.

11. The method of claim 1, wherein said acidic solution in step (a) comprises an acid that can produce a sufficient concentration of positive hydrogen ions (H+) in solution that can displace adsorbed metal ions in the fluidic path.

12. The method of claim 1, wherein said acidic solution in step (a) comprises a weak acid.

13. The method of claim 12, wherein said weak acid is selected from the group consisting of formic acid, acetic acid, propionic acid, butyric acid, valeric acid, caprioic acid, lactic acid, malic acid, citric acid, benzoic acid, carbonic acid, trichloroacetic acid, hydrofluoric acid, hydrocyanic acid, oxalic acid, sulfurous acid, hydrogen sulfate ion, phosphoric acid and nitrous acid.

14. The method of claim 1, wherein step (a) is carried out for 1 minute, 2 minutes, 3 minutes, 5 minutes, 10 minutes or 15 minutes.

15. The method of claim 1, wherein step (a) is carried out for less than 1 minute.

16. The method of claim 1, wherein said negatively charged analyte is a nucleic acid or a derivative or analog thereof.

17. The method of claim 16, wherein said nucleic acid is an oligonucleotide.

18. The method of claim 17, wherein said oligonucleotide is an aptamer or an RNAi.

19. The method of claim 17, wherein said oligonucleotide is Formivirsen (Vitravene) or pegaptinib (Macugen).

* * * * *